United States Patent [19]
Torossian

[11] Patent Number: 5,851,210
[45] Date of Patent: Dec. 22, 1998

[54] STENT DELIVERY SYSTEM AND METHOD

[76] Inventor: Richard Torossian, 1 Blueberry Rd., Windham, N.H. 03087

[21] Appl. No.: 822,162

[22] Filed: Mar. 21, 1997

[51] Int. Cl.$^6$ .................................................. A61F 11/00
[52] U.S. Cl. ............................. 606/108; 606/198; 604/96
[58] Field of Search ................................ 606/1, 106, 108, 606/113, 127, 151, 191–200; 604/96–104, 264

[56] References Cited

U.S. PATENT DOCUMENTS

| | | | |
|---|---|---|---|
| 4,990,139 | 2/1991 | Jang | 604/101 |
| 5,002,532 | 3/1991 | Gaiser et al. | 604/101 |
| 5,071,406 | 12/1991 | Jang | 604/96 |
| 5,261,878 | 11/1993 | Galindo | 604/96 |
| 5,318,535 | 6/1994 | Miraki | 604/102 |
| 5,320,605 | 6/1994 | Sahota | 604/101 |
| 5,415,635 | 5/1995 | Bagaoisan et al. | 604/96 |
| 5,423,742 | 6/1995 | Theron | 604/28 |
| 5,445,646 | 8/1995 | Euteneuer, et al. | 606/198 |
| 5,456,694 | 10/1995 | Marin et al. | 606/198 |
| 5,458,573 | 10/1995 | Summers | 604/101 |
| 5,460,610 | 10/1995 | Don Michael | 604/101 |
| 5,478,349 | 12/1995 | Nicholas | 606/198 |
| 5,498,238 | 3/1996 | Shapland et al. | 604/53 |
| 5,514,092 | 5/1996 | Forman et al. | 604/101 |
| 5,549,554 | 8/1996 | Miraki | 604/101 |
| 5,632,760 | 5/1997 | Sheiban et al. | 606/198 |

*Primary Examiner*—Glenn K. Dawson
*Attorney, Agent, or Firm*—Bourque & Associates P.A.

[57] ABSTRACT

A stent deployment system includes a delivery catheter, a dilation balloon disposed at the distal end of the delivery catheter, and a stent deployment mechanism disposed at a predetermined distance from the dilation balloon. The delivery catheter includes a plurality of markers at the proximal end that are used to gauge the movement of the delivery catheter and to align the dilation balloon and stent deployment mechanism with a target region in a vessel, such as a lesion or blocked region. The stent deployment method includes introducing the delivery catheter into the vessel until the dilation balloon is aligned with the target region, and inflating the dilation balloon to predilate the target region. The delivery catheter is then advanced until the stent deployment mechanism is aligned with the predilated target region using the markers on the proximal end of the delivery catheter. When properly aligned with the predilated target region, the stent deployment mechanism deploys the stent against the target region of the vessel. The delivery catheter is then withdrawn until the dilation balloon is again aligned with the stent deployed in the target region, and the dilation balloon is inflated to post-dilate or further embed the stent into the target region of the vessel.

21 Claims, 4 Drawing Sheets

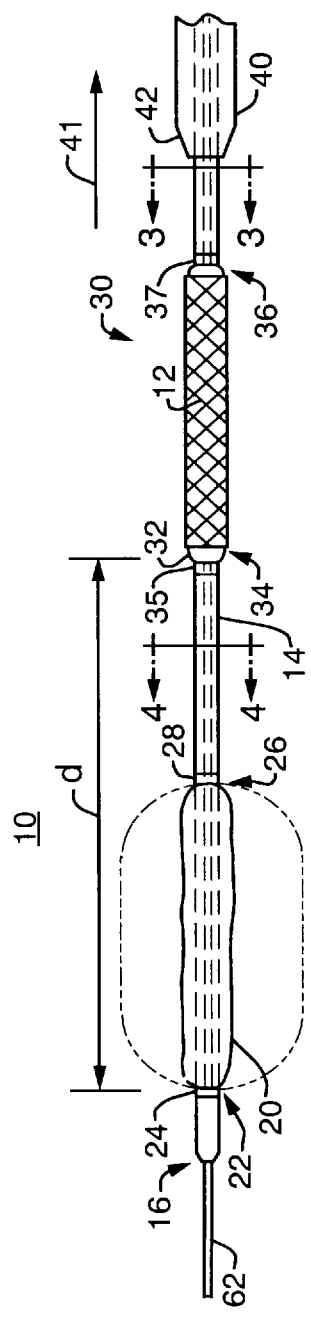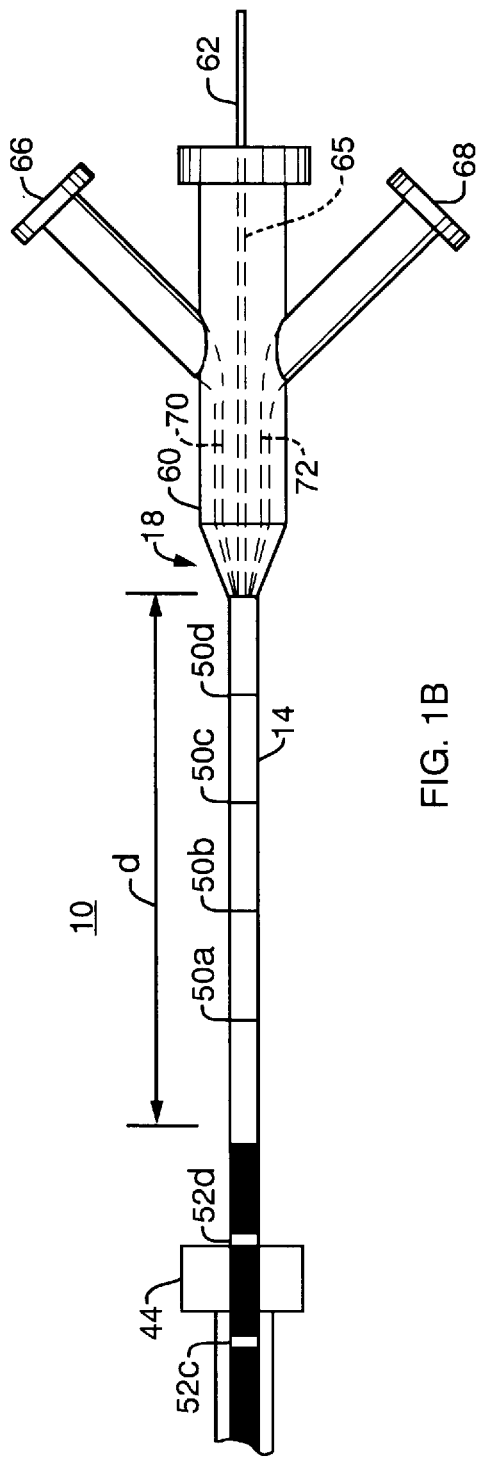
FIG. 1A
FIG. 1B

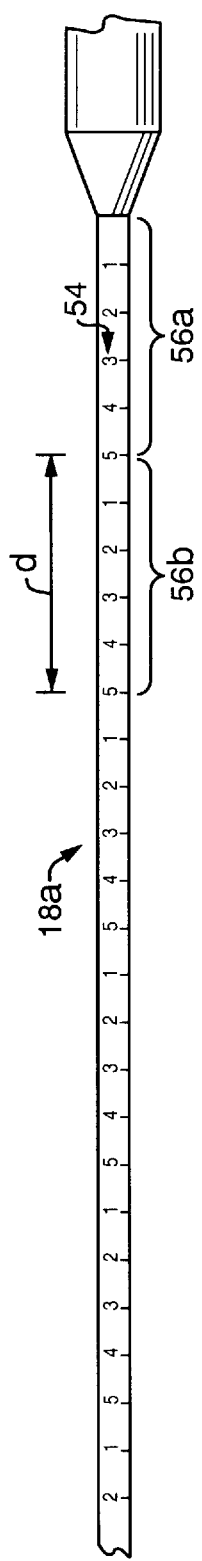
FIG. 2
FIG. 4
FIG. 3

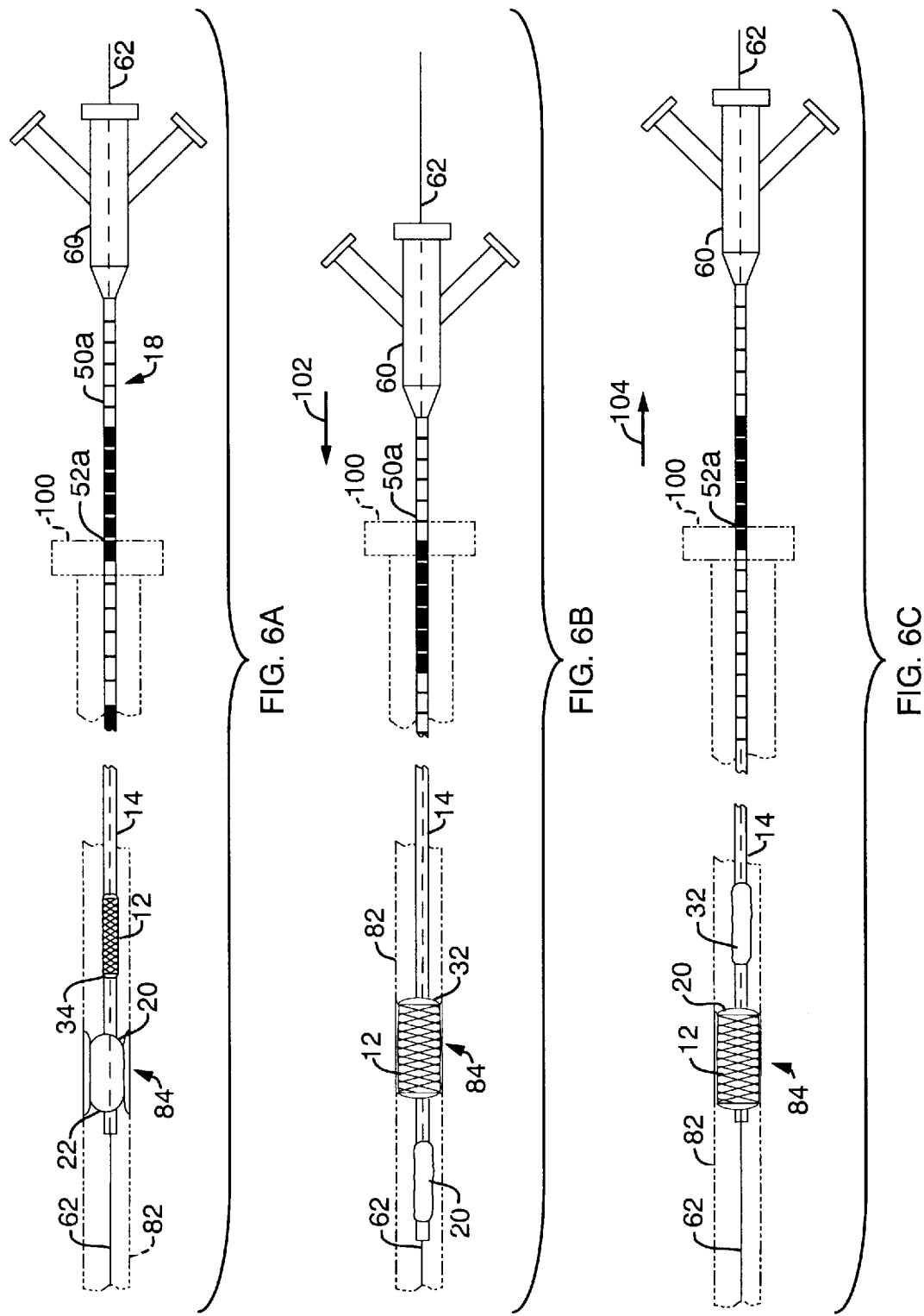

STENT DELIVERY SYSTEM AND METHOD

FIELD OF THE INVENTION

The present invention relates to a system, and method for delivering intraluminal devices and more particularly, to a system and method for delivering an intravascular stent to a diseased or occluded blood vessel.

BACKGROUND OF THE INVENTION

Heart disease has been one of the leading causes of death and an increasing health concern. One cause of heart disease is occluded or blocked coronary arteries in which the flow of blood to the heart is impeded. Various systems and methods have emerged for treating diseased or occluded arteries or other vessels. One procedure involves bypass surgery which requires anesthesia, cutting of the chest wall, and surgical removal of the blocked region in the vessel (also called an occlusion, stenosis, or lesion).

A less invasive procedure called percutaneous transluminal coronary angioplasty (PTCA) opens the vessel to increase the blood flow through the vessel without having to cut through the patient's chest. According to this procedure, a catheter having a small balloon at the far or distal end is advanced into the patient's coronary artery to the target region containing the blockage. The balloon is aligned without the target region of the diseased artery using standard x-ray fluoroscopy techniques. When aligned with the blockage, the balloon is inflated within the patient's artery to open up the arterial passageway. The dilation balloon is typically inflated one or more times until the target region of the vessel is sufficiently dilated. The balloon catheter is then withdrawn from the vessel.

Dilation of an occluded artery using PTCA, however, is often only a temporary treatment. Commonly, restenosis occurs when the target region of the dilated vessel narrows and the blockage returns, again restricting flow of blood through the vessel. The PTCA procedure must often be performed again to maintain a healthy flow of blood through the diseased artery.

One solution to the problem of restenosis has been to deploy an intraluminal device, such as an intravascular stent, to the target region of the vessel. The intravascular stent opens the passageway of the vessel and is left in the vessel to maintain the open passageway, thereby preventing restenosis or a recurrence of blockage at the target region of the vessel. This procedure, often called "stenting," provides a longer lasting treatment to the diseased blood vessels.

One type of stent delivery system includes a catheter having a delivery balloon and an expandable stent disposed around the delivery balloon. When the stent is aligned with the blockage in the target region of the vessel, the delivery balloon is inflated to expand the stent against the target region of the vessel. When the catheter is withdrawn, the stent is left in the vessel to maintain the open passageway of the vessel and prevent restenosis.

A typical method for delivering the stent requires the target region of the vessel to be predilated to confirm the distensibility or ability of the target region to expand and to open the target region allowing the stent delivery mechanism to cross the target region without causing further damage. Predilation is performed using a separate balloon catheter having a dilation balloon that is introduced through the vessel to the target region. The predilation balloon is aligned with the target region using x-ray fluoroscopy to identify radiopaque markers disposed on either side of the balloon. The dilation balloon is inflated to predilate the target region, following which the balloon catheter is withdrawn from the vessel.

The stent delivery catheter is then introduced into the target blood vessel and an attempt is made to accurately align the stent with the predilated target region of the vessel. Fluoroscopy or digital recording is used again to align radiopaque markers on both sides of the stent with the target region of the vessel and often must be repeated numerous times for proper alignment. Once properly aligned, the stent is deployed, for example, by inflating the stent delivery balloon and expanding the stent against the walls of the target region in the vessel. The stent delivery catheter is then withdrawn from the vessel.

A post-dilation step is often required to further imbed the stent into the target region of the vessel. This is accomplished by inserting yet another balloon catheter into the vessel until the dilation balloon is aligned with the stent using fluoroscopy or digital recording. The post dilation balloon is expanded against the stent to further secure the stent into the target region of the vessel. This step is often repeated one or more times as necessary.

Although the above procedure is generally effective at deploying a stent in the target region of a vessel, a number of drawbacks exist. To perform the three stages of this procedure—predilation, stent deployment, and post dilation—three separate catheters must be inserted, deployed and retracted, resulting in a time consuming and expensive procedure. Every time a separate catheter must be introduced into the patient, the patient is subject to inherent risks. In particular, when the post dilation balloon catheter is advanced over the stent, the tip of the post dilation balloon catheter could catch on the stent, preventing the post dilation of the stent. The patient and medical staff are also subjected to radiation each time x-ray fluoroscopy is used and even higher doses of radiation when digital recording is used to locate and align each of the three catheters within the vessel. Moreover, the alignment of the dilation balloons and the stent delivery mechanism using fluoroscopy relies on the visual recognition of the radiopaque markers within the artery which is often difficult.

Accordingly, a need exists for a stent delivery system and method that is more accurate, less invasive to the patient, that reduces the amount of time to perform the procedure, that reduces the cost of the procedure, and that reduces the amount of radiation needed to locate and align the catheter balloons. A need exists for a stent delivery system in which a single catheter is used to perform all three steps—predilation, stent deployment, and post dilation—with a simple and effective alignment within the target region of the vessel.

SUMMARY OF THE INVENTION

The present invention features a stent delivery system for delivering a stent to a target region in a vessel. The stent delivery system comprises a delivery catheter having a distal end and a proximal end. The distal end of the delivery catheter extends through the vessel to the target region in the vessel. At least one dilation balloon is disposed on the delivery catheter proximate to the distal end of the delivery catheter, for predilating the target region of the vessel. A stent deployment mechanism is disposed on the delivery catheter proximate to the dilation balloon, for deploying a stent to the target region of the vessel that has been predilated by the dilation balloon. A leading end of the stent deployment mechanism is disposed at a predetermined distance from the leading end of the dilation balloon.

The delivery catheter preferably includes at least one set of markers disposed near the proximal end of the delivery catheter. The set of markers provides an indication of the predetermined distance between the leading end of the stent delivery mechanism and the leading end of dilation balloon, for gauging movement of the dilation balloon and the stent delivery mechanism into alignment with the target region in the vessel.

According to a preferred embodiment, at least one set of a first type of markers and at least one set of a second type of markers are disposed adjacent one another in the region of the proximal end of the delivery catheter. Each set of a first type of markers and each set of a second type of markers has a predetermined length corresponding to the predetermined distance between the leading end of the dilation balloon and the leading end of the stent delivery mechanism and includes a predetermined number of markers evenly spaced within the predetermined length. The distance between one of the first type of markers in one set and a corresponding one of the second type of markers in an adjacent set corresponds to the predetermined distance between the leading end of the dilation balloon and the leading end of the stent delivery mechanism. Preferably, a plurality of sets of the first type of markers alternate with a plurality of sets of the second type of markers.

In accordance with one embodiment of the present invention, the first type of markers has a first color and the second type of markers has a second color, for distinguishing between the first type of markers and the second type of markers. In accordance with another embodiment, the set of markers includes at least first and second sets of indicia disposed adjacent one another on the delivery catheter.

The dilation balloon is preferably a high pressure balloon, such as a generally cylindrical, non-compliant balloon having an expanded diameter of about 2.5 to 4.0 mm, for predilating the target region of the vessel and for further embedding the stent in the vessel at the target region. One type of stent deployment mechanism includes a stent deployment balloon, such as a low pressure balloon, for expanding the stent, such as an expandable metal stent, disposed over the stent deployment balloon. The delivery catheter preferably includes a dilation balloon flow passage, for inflating the dilating balloon, and a stent deployment balloon flow passage, for independently inflating the stent deployment balloon.

The present invention also features a method of delivering a stent to a target region in a vessel using the stent delivery system defined above. The method comprises the steps of: guiding the distal end of the delivery catheter through the vessel to the target region of the vessel; moving the delivery catheter until the dilation balloon is aligned with the target region of the vessel; inflating the dilation balloon, for predilating the target region of the vessel; moving the delivery catheter until the stent deployment mechanism is aligned with the target region of the vessel; deploying a stent to the target region of the vessel; and withdrawing the delivery catheter from the vessel.

The step of guiding the distal end of the delivery catheter preferably includes: inserting a guide catheter into the vessel until a distal end of the guide catheter is disposed proximate to the target region of the vessel; and inserting the delivery catheter into the guide catheter until the distal end of the delivery catheter is disposed proximate the target region of the vessel.

The step of moving the delivery catheter until the stent deployment mechanism is aligned with the target region of the vessel includes moving the delivery catheter the predetermined distance between the leading end of the dilation balloon and the leading end of the balloon deployment mechanism. One of the plurality of markers is preferably aligned with a fixed alignment member, such as the guide catheter, and the delivery catheter is moved until the corresponding one of the next set of markers is aligned with the fixed alignment member.

The preferred method further includes, after the step of deploying the stent, moving the delivery catheter until the dilation balloon is aligned with the stent and inflating the dilation balloon, for further embedding the stent into the vessel.

BRIEF DESCRIPTION OF THE DRAWINGS

These and other features and advantages of the present invention will be better understood by reading the following detailed description, taken together with the drawings wherein:

FIGS. 1A and 1B are a side view of a stent delivery system according to one embodiment the present invention;

FIG. 2 is a side view of a proximal end of a delivery catheter having a plurality of indicia markers according to another embodiment of the present invention;

FIG. 3 is a cross-sectional view of the delivery catheter of the stent delivery system taken along line 3—3 of FIG. 1A;

FIG. 4 is a cross-sectional view of the delivery catheter of the stent delivery system taken along line 4—4 of FIG. 1A;

FIG. 6A is a side, partially cross-sectional view of the predilation of the target region in the vessel using the stent delivery method according to the present invention;

FIG. 6B is a side, partially cross-sectional view of the deployment of the stent using the stent delivery method according to the present invention; and FIG. 6C is a side, partially cross-sectional view of the post dilation of the stent using the stent delivery method of the present invention.

DETAILED DESCRIPTION OF THE PREFERRED EMBODIMENT

Figure 5:
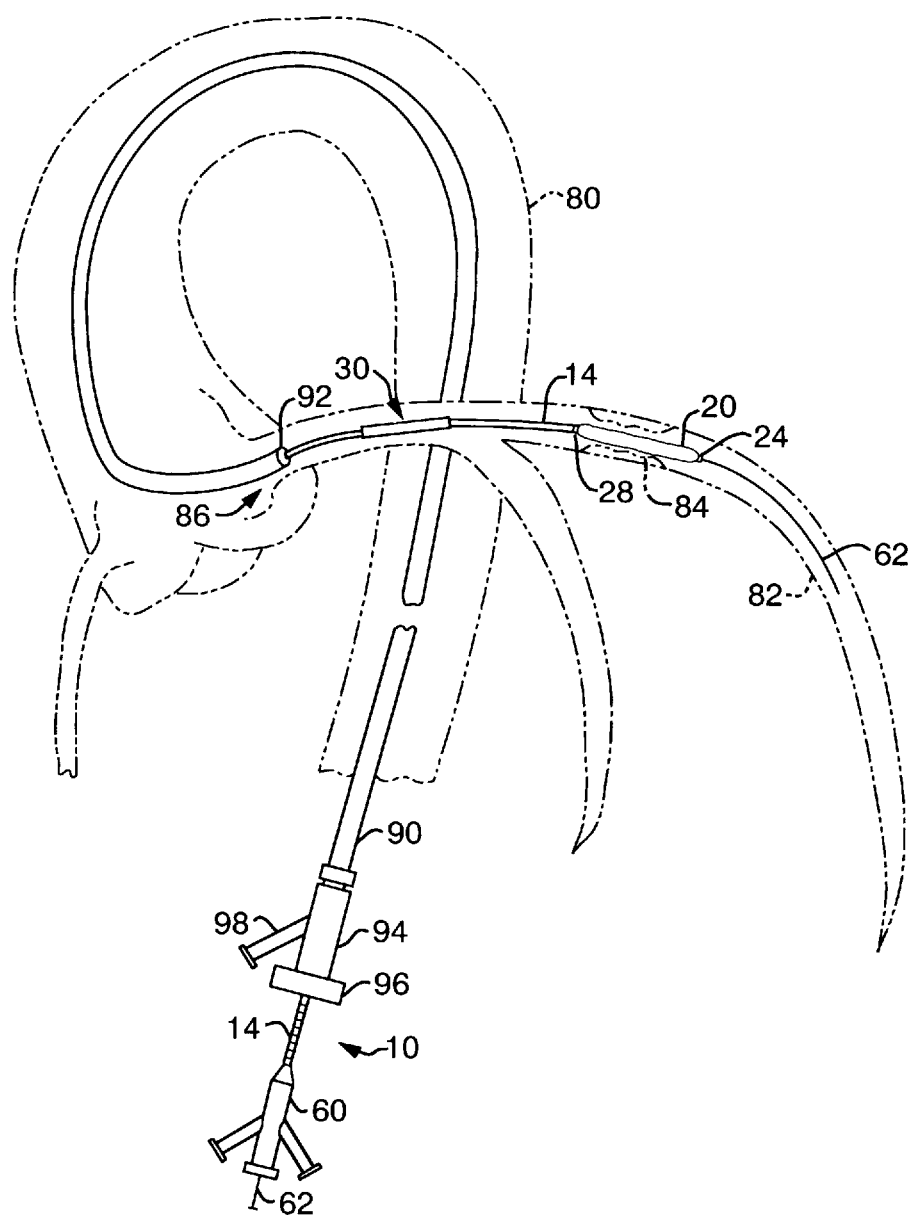
FIG. 5 is a simplified cross-sectional view of the stent delivery system introduced through a guiding catheter to a target region of a coronary vessel.

A stent delivery system 10, FIGS. 1A and 1B, according to the present invention, is used to deliver a stent 12 to a target region in a blood vessel or other body lumen. According to the exemplary embodiment, the stent 12 is delivered to an occluded or blocked region of a diseased artery (also called a stenosis or lesion). The present invention, however, contemplates using the stent delivery system 10 to delivery and secure the stent 12 or other types of intraluminal devices within other types of vessels or body lumens. One type of stent 12 includes an intravascular expandable stent formed as a slotted tube of stainless steel, such as a PALMAZ-SCHATZ™ brand stent manufactured by Johnson & Johnson Interventional Systems Co. The present invention also contemplates other types of self-expanding or non self-expanding stents, biological stents, and other types of intraluminal devices known to those of ordinary skill in the art.

The stent delivery system 10 includes a delivery catheter 14 having a distal end 16 (FIG. 1A) adapted to extent through the vessel to the target region of the vessel and a proximal end 18 (FIG. 1B) that is maneuvered by the physician performing the procedure. A dilation balloon 20 is disposed on the delivery catheter 14 proximate to the distal end 16, for predilating and/or post-dilating the target region of the vessel, and a stent deployment mechanism 30 is disposed proximate to the dilation balloon 20 on the delivery catheter 14, for deploying the stent 12 to the target region of the vessel, as will be described in greater detail below.

The dilation balloon 20 has a leading end 22 with a first radiopaque marker 24 and a trailing end 26 with a second radiopaque marker 28. The first and second radiopaque markers 24, 28 are used to locate the dilation balloon 20 at the target region of the vessel using standard fluoroscopy techniques. One example of the dilation balloon 20 is a high pressure, non-compliant balloon typically used for PTCA dilations of a vessel. The dilation balloon 20 preferably has a cylindrical shape with an expanded diameter in the range of about 2.5 to 4.0 mm and is made of a polymer such as polyvinylchloride (PVC), PET, nylon, various derivatives of polyethylene, or other suitable material. The length of the dilation balloon 20 preferably generally corresponds to the length of the stent 12. The present invention contemplates more than one dilation balloon 20 of varying sizes on a single delivery catheter 14, for predilating target regions of different diameters and lengths.

The stent deployment mechanism 30 preferably includes a stent deployment balloon 32 having a leading end 34 and a trailing end 36. The stent deployment balloon 32 is preferably a low pressure, compliant balloon having a substantially cylindrical shape with an expanded diameter in the range of about 2.5 to 4.0 mm and made of a polyethylene or other suitable material. The stent delivery balloon 32 is inflated to cause the stent 12 to expand. The stent deployment mechanism 30 also has a first radiopaque marker 35 at the leading end 34 of the deployment balloon 32 and a second radiopaque marker 37 at the trailing end 36 of the deployment balloon 32, for use in verifying the alignment of the stent deployment mechanism 30 with the target region, if necessary. The length of the stent 12 and stent deployment balloon 32 can vary depending upon the size of the vessel and target region to be treated. The present invention also contemplates using a non-compliant balloon as the stent delivery balloon.

A protective sheath 40, preferably made of a translucent material, is optionally provided to cover and protect the stent deployment mechanism 30 when moving through the vessel and across the target region. The protective sheath 40 is retracted to expose the stent deployment mechanism 30 prior to deploying the stent (shown in the retracted position in FIG. 1A). The protective sheath 40 preferably has a tapered end 42 that passes through the vessel and across the target region without damaging the vessel. At the proximal end, the protective sheath 40 has a sheath adapter 44, FIG. 1B, that secures the protective sheath 40 to the delivery catheter 14.

The leading end 22 of the dilation balloon 20 is disposed at a predetermined distance d from the leading end 34 of the stent deployment mechanism 30. In one example, the predetermined distance d is in a range of about 25–45 mm. At the proximal end 18 of the delivery catheter 14 (FIG. 1B), the stent delivery system 10 includes a plurality of markers 50, 52 used to gauge the movement of the delivery catheter 14 through the vessel.

The markers 50a–50d, 52a–52d preferably include a set of a first type of markers 50 and an adjacent set of a second type of markers 52 that are distinguishable from the first type of markers 50, e.g. a different color. Each set of the first or second type of markers 50a–50d, 52a–52d has an overall length corresponding to the predetermined distance d between the leading end 22 of the dilation balloon 20 and the leading end 34 of the stent deployment mechanism 30. Each set includes a predetermined number of evenly spaced markers such that the distance between a marker 50d in one set and a corresponding marker 52d on the adjacent set is the same as the predetermined distance between the dilation balloon 20 and stent deployment mechanism 30. The markers 50a–50d, 52a–52d are used to gauge the movement of the delivery catheter 14 between the dilation balloon 20 and stent deployment mechanism 30 to provide alignment with the target region of the vessel, as will be described in greater detail below.

According to an alternative embodiment of the delivery catheter 14, FIG. 2, of the present invention, the proximal end 18a includes markers having indicia 54, such as numeric indicia. The indicia 54 are preferably arranged in sets 56a, 56b each set having a length corresponding to the predetermined distance d between the leading end of the dilation balloon and the leading end of the stent deployment mechanism. For example, each set 56a, 56b of indicia can include numerals 1–5 such that the distance between a numeral in one set 56a and a corresponding numeral in an adjacent set 56b corresponds to the predetermined distance d. The present invention also contemplates other types of markers or indicia used to gauge the movement of the delivery catheter 14 and align the dilation balloon and stent deployment mechanism with the target region of the vessel.

The stent delivery system 10 (FIG. 1B) preferably includes a catheter adapter 60, such as a Y-adapter, connected to the delivery catheter 14 at the proximal end 18. One type of stent delivery system 10 also includes a guide wire 62 extending into the catheter adapter 60, through a central lumen 65 of the delivery catheter 14, and out of the delivery catheter 14 at the distal end 16. The guide wire is typically made of a stainless steel or other suitable material and has a diameter in a range of about 0.014 to 0.018 inches. The delivery catheter 14 slides over the guide wire 62 to guide the delivery catheter 14 through the vessel.

The catheter adapter 60 further includes a dilation balloon port 66 and a deployment balloon port 68, for independently inflating the dilation balloon 20 and stent deployment balloon 32 respectively. The dilation balloon port 66 fluidly couples a source of pressurized fluid (not shown), such as dye, to a dilation balloon lumen or passageway 70 extending through the catheter adapter 60 and the delivery catheter 14 to the dilation balloon 20 as is well known in the art. Discharging the pressurized fluid into the dilation balloon port 66 causes the dilation balloon 20 to be inflated. The deployment balloon port 68 fluidly couples a source of pressurized fluid to a deployment balloon lumen or passageway 72 that extends through the catheter adapter 60 and delivery catheter 14 to the deployment balloon 32.

Discharging the pressurized fluid into the deployment balloon port 68 causes the deployment balloon 32 to be inflated and the expandable stent 12 to be deployed.

Within the delivery catheter 14, FIGS. 3 and 4, the deployment balloon passageway 72 extends to the deployment balloon 32, the dilation balloon passageway 70 extends to the dilation balloon 20, and the central passageway 65 extends through the entire delivery catheter 14. The delivery catheter 14 is typically made of a nylon, kevlar, PET or other suitable material and has a diameter in a range of about 3.7 F (French size) proximal to 2.0 F distal and a length in a range of about 135 cm. Although the exemplary embodiment shows a solid delivery catheter 14 having passageways 65, 70, 72 formed therein, the present invention also contemplates other types of passageways of lumens formed in the catheter as known in the art.

According to the method of the present invention, the stent delivery system 10, FIG. 5, is introduced into a vessel 80, such as the brachial or femoral arteries, to a diseased vessel 82, such as a coronary artery. According to a preferred method, a guide catheter 90 is first introduced into the vessel 80 until a distal end 92 of the guide catheter 90 is disposed at the opening 86 of the diseased vessel 82. Next, the guide wire 62 is advanced through the guide catheter 90 and the vessel 82 until the guide wire 62 passes beyond the target region 84 of the vessel 82. The distal end 16 of the delivery catheter 14 is then slid over the guide wire 62, inserted into the guide catheter 90 and advanced through the guide catheter 90. The guide catheter 90 guides the delivery catheter 14 to the opening 86 of the vessel 82, after which the guide wire 62 then guides the delivery catheter 14 into the vessel 82 until the dilation balloon 20 is aligned with the target region 84. The dilation balloon 20 is initially aligned using the radiopaque markers 24, 28 and standard fluoroscopy techniques known to those skilled in the art.

The guide catheter 90 preferably includes a catheter adapter 94 having a catheter engagement mechanism 96, such as a hemostasis valve, that engages the delivery catheter 14 and prevents movement of the delivery catheter 14 relative to the guide catheter 90 when the dilation balloon 20 is aligned at the target region 84. The adapter 94 preferably has a Y-configuration with a port 98 for injecting fluid through the guide catheter 90 to the target region 84. The stent delivery system 10 shown in FIG. 5 does not include the optional protective sheath 40 and sheath adapter 44 shown in FIGS. 1A and 1B. If the protective sheath 40 is provided over the delivery catheter 14, the delivery catheter 14 and protective sheath 40 are passed through the guide catheter 90 together with the protective sheath 40 covering the stent deployment mechanism 30. The engagement mechanism 96 of the guide catheter 90 engages the protective sheath 40, and the sheath adapter 44 in turn engages the delivery catheter 14 (see FIG. 1B). When the dilation balloon 20, FIG. 6A, is aligned with the target region 84 of the vessel 82, the dilation balloon 20 is inflated to predilate the target region 84. The dilation balloon 20 is preferably inflated with a pressure in the range of 2–15 atm and for a period of time of about 30 s, sufficient to dilate the target region 84 of the vessel 82. The predilation may be repeated as necessary to sufficiently open the target region 84 to allow passage of the stent delivery mechanism 30.

When the dilation balloon 20 is aligned with the target region 84, one of the markers 52a near the proximal end of the delivery catheter 14 is aligned with a fixed alignment member 100, such as the hemostasis valve 96 of the guide catheter 90. If a protective sheath 40 is used, the marker 52a can be observe throught the translucent protective sheath 40 and aligned with the hemostasis valve 96 of the guide catheter.

When predilation is completed, the delivery catheter 14, FIG. 6B, is advanced in the direction of arrow 102 to align the stent 12 across the predilated target region 84. The delivery catheter 14 is moved with respect to the fixed alignment member 100 until a corresponding marker 50a on an adjacent set of markers is aligned with the fixed alignment member 100. Since the distance between the markers 52a, 50a of the adjacent sets of markers corresponds to the predetermined distance between the leading end 22 of the dilation balloon 20 and the leading end 34 of the stent deployment mechanism 30, the stent 12 can be precisely aligned with the target region 84 using the markers 52a, 50a. Although alignment is made using the markers 50a, 52a, fluoroscopy can optionally be utilized if the proper alignment of the stent 12 must be further verified.

When the stent 12 is aligned with the target region 84, the stent deployment balloon 32 is inflated to expand the stent 12 against the walls of the vessel 82 at the target region 84. Typically, pressure is gradually applied to the stent deployment balloon 32 until a maximum pressure is reached in a range of about 6 to 8 atm and for a period of time of about 15 to 60 seconds. If a protective sheath (not shown) is used, the stent 12 is covered with the protective sheath when moved across the target region 84. When properly aligned with the target region 84, the protective sheath is retracted to expose the stent 12 prior to deployment.

After deployment of the stent 12, FIG. 6C, the delivery catheter 14 is withdrawn in the direction of arrow 104 until the first marker 52a is aligned with the fixed alignment member 100, thereby aligning the dilation balloon 20 with the stent 12 deployed at the target region 84. The dilation balloon 20 is then inflated to post-dilate or further embed the stent 12 into the target region 84 of the vessel 82. After post dilation, the dilation balloon 20 is deflated and the delivery catheter 14 is withdrawn from the vessel 82. Post dilation is often repeated at higher pressures to assure that all stent struts are expanded against the wall of the vessel and to open the vessel further.

Accordingly, the three steps of predilation, stent deployment, and post dilation are performed using a single delivery catheter in less time than if three separate catheters were introduced into the vessel of the patient. Using a single delivery catheter in the stent delivery system and method of the present invention is less invasive to the patient and reduces the amount of radiation used during fluoroscopy to locate the balloon at the target region. By reducing the number of catheters that must be introduced into the vessel of the patient, the risk of damaging the vessel is also reduced.

Modifications and substitutions by one of ordinary skill in the art are considered to be within the scope of the present invention which is not to be limited except by the claims which follow.

What is claimed is:

1. A stent delivery system, for delivering a stent to a target region in a vessel, said stent delivery system comprising:

a delivery catheter having a distal end and a proximal end, wherein said distal end of said delivery catheter is adapted to extend through said vessel to said target region in said vessel;

at least one dilation balloon disposed on said delivery catheter proximate to said distal end of said delivery catheter, for pre-dilating said target region of said vessel, said dilation balloon having a leading end and a trailing end;

a stent deployment mechanism disposed on said delivery catheter proximate to said dilation balloon, for deploying a stent to said target region of said vessel that has been pre-dilated by said dilation balloon, said stent deployment mechanism having a leading end and trailing end, wherein said leading end of said stent deployment mechanism is disposed at a predetermined distance from said leading end of said dilation balloon; and said delivery catheter including at least one set of markers disposed proximate to said proximal end of said delivery catheter, wherein said at least one set of markers provides an indication of said predetermined distance between said leading end of said stent delivery mechanism and said leading end of said dilation balloon, for gauging movement of said dilation balloon and said stent delivery mechanism into alignment with said target region in said vessel.

2. The stent delivery system of claim 1 wherein said at least one set of markers includes at least one set of a first type of markers and at least one adjacent set of a second type of markers disposed proximate to said proximal end of said delivery catheter, wherein said second type of markers is visually distinguishable from said first type of markers, and wherein said at least one set of a first type of markers and said at least one adjacent set of a second type of markers have a predetermined length corresponding to said predetermined distance between said leading end of said dilation balloon and said leading end of said stent delivery mechanism.

3. The stent delivery system of claim 2 wherein each of said at least one set of a first type of markers and said at least one adjacent set of a second type of markers include a corresponding predetermined number of markers evenly spaced within said predetermined length, wherein the distance between one of said first type of markers in said one set and a corresponding one of said second type of markers in said adjacent set corresponds to said predetermined distance between said leading end of said dilation balloon and said leading end of said stent delivery mechanism.

4. The stent delivery system of claim 2 wherein said first type of markers has a first color and said second type of markers has a second color, for visually distinguishing said first type of markers and said second type of markers.

5. The stent delivery system of claim 2, wherein said at least one set of a first type of markers and said at least one adjacent set of a second type of markers include a plurality of sets of said first type of markers alternating with a plurality of sets of said second type of markers.

6. The stent delivery system of claim 1 wherein said at least one set of markers includes at least first and second adjacent sets of indicia disposed on said delivery catheter, wherein a distance between one of said first adjacent set of indicia and a corresponding one of said second adjacent set of indicia corresponds to said predetermined distance between said leading end of said dilation balloon and said leading end of said stent delivery mechanism.

7. The stent delivery system of claim 1 wherein said dilation balloon is a high pressure balloon, for pre-dilating said target region of said vessel and for further embedding said stent in said vessel at said target region.

8. The stent delivery system of claim 1 wherein said dilation balloon is generally cylindrical in shape.

9. The stent delivery system of claim 1 wherein said dilation balloon has an expanded diameter of between 2.5 to 4.0 mm.

10. The stent delivery system of claim 1 wherein said stent deployment mechanism includes a stent deployment balloon, for expanding said stent disposed over said stent deployment balloon.

11. The stent delivery system of claim 10 wherein said stent includes an expandable metal stent disposed over said stent deployment balloon.

12. The stent delivery system of claim 10 wherein said delivery catheter includes a dilation balloon flow passage, for inflating said dilation balloon, and a stent deployment balloon flow passage, for independently inflating said stent deployment balloon.

13. A method of delivering a stent to a target region in a vessel using a stent delivery system having a delivery catheter, a dilation balloon disposed proximate to a distal end of said delivery catheter, and a stent deployment mechanism disposed proximate to said dilation balloon, said method comprising the steps of:
  guiding said distal end of said delivery catheter through said vessel to said target region of said vessel;
  moving said delivery catheter until said dilation balloon is aligned with said target region of said vessel;
  inflating said dilation balloon, for pre-dilating said target region of said vessel;
  moving said delivery catheter until said stent deployment mechanism is aligned with said target region of said vessel;
  deploying a stent to said target region of said vessel;
  moving said delivery catheter until said dilation balloon is aligned with said stent;
  inflating said dilation balloon, for further embedding said stent into said vessel; and
  withdrawing said delivery catheter from said vessel.

14. The method of claim 13 wherein the step of deploying said stent to said target region in said vessel includes inflating a stent deployment balloon, for expanding said stent into engagement with said vessel.

15. The method of claim 13 wherein a leading end of said stent deployment mechanism is disposed a predetermined distance from a leading end of said dilation balloon, and wherein the step of moving said delivery catheter until said stent deployment mechanism is aligned with said target region of said vessel includes moving said delivery catheter said predetermined distance between said leading end of said dilation balloon and said leading end of said balloon deployment mechanism.

16. The method of claim 13 wherein said step of guiding said distal end of said delivery catheter includes:
  inserting a guide catheter into said vessel until a distal end of said guide catheter is disposed proximate to said target region of said vessel; and
  inserting said delivery catheter into said guide catheter until said distal end of said delivery catheter is disposed proximate said target region of said vessel.

17. The method of claim 13 wherein said delivery catheter includes a plurality of markers disposed proximate a proximal end of said delivery catheter, wherein a distance between one of said plurality of markers and a corresponding one of said plurality of markers corresponds to a predetermined distance between said leading end of said dilation balloon and a leading end of said stent deployment mechanism.

18. The method of claim 17 wherein said one of said plurality of markers is aligned with a fixed alignment member when said dilation balloon is aligned with said target region in said vessel, and wherein the step of moving said delivery catheter until said stent deployment mechanism is aligned with said target region of said vessel includes moving said delivery catheter until said corresponding one of said plurality of markers is aligned with said fixed alignment member.

19. A stent delivery system, for delivering a stent to a target region in a vessel, said stent delivery system comprising:
  a delivery catheter having a distal end and a proximal end, wherein said distal end of said delivery catheter is adapted to extend through said vessel to said target region in said vessel;
  at least one dilation balloon disposed on said delivery catheter proximate to said distal end of said delivery catheter, for pre-dilating said target region of said vessel, said dilation balloon having a leading end and a trailing end;

a stent deployment balloon disposed on said delivery catheter proximate to said dilation balloon, for deploying a stent to said target region of said vessel that has been pre-dilated by said dilation balloon, said stent deployment balloon having a leading end and a trailing end, wherein a point on said stent deployment balloon is disposed at a predetermined distance from a point on said dilation balloon; and wherein said delivery catheter includes at least one set of markers disposed proximate said proximal end of said delivery catheter, for providing an indication of said predetermined distance between said stent deployment balloon and said dilation balloon and for gauging movement of said dilation balloon and said stent deployment balloon into alignment with said target region in said vessel.

20. The stent delivery system of claim 19 in combination with a stent, said stent disposed on said stent deployment balloon, wherein a length of said dilation balloon is substantially equal to a length of said stent, for further embedding said stent deployed at said target region of said vessel.

21. The stent delivery system of claim 19 further including a guide catheter for receiving said delivery catheter, said guide catheter having a proximal end adapted to align with at least one of said markers, for gauging movement of said dilation balloon and said stent delivery balloon into alignment with said target region in said vessel.

* * * * *